(12) United States Patent
Elsner et al.

(10) Patent No.: US 7,831,106 B2
(45) Date of Patent: Nov. 9, 2010

(54) LASER SCANNING DIGITAL CAMERA WITH SIMPLIFIED OPTICS AND POTENTIAL FOR MULTIPLY SCATTERED LIGHT IMAGING

(75) Inventors: Ann E. Elsner, Bloomington, IN (US); Benno Petrig, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 48 days.

(21) Appl. No.: 12/302,531

(22) PCT Filed: May 30, 2007

(86) PCT No.: PCT/US2007/012726

§ 371 (c)(1),
(2), (4) Date: Jun. 3, 2009

(87) PCT Pub. No.: WO2007/142960

PCT Pub. Date: Dec. 13, 2007

(65) Prior Publication Data

US 2009/0244482 A1     Oct. 1, 2009

Related U.S. Application Data

(60) Provisional application No. 60/809,551, filed on May 31, 2006.

(51) Int. Cl.
*G06K 9/40* (2006.01)
(52) U.S. Cl. .................. 382/254; 382/274; 382/275; 382/282
(58) Field of Classification Search ................. 382/254, 382/274, 275, 282
See application file for complete search history.

(56) References Cited

U.S. PATENT DOCUMENTS

| | | | |
|---|---|---|---|
| 4,838,679 A | 6/1989 | Bille | |
| 5,583,795 A | 12/1996 | Smyth | |
| 5,895,415 A | 4/1999 | Chow et al. | |
| 6,061,092 A | 5/2000 | Bakhle et al. | |
| 6,120,461 A | 9/2000 | Smyth | |
| 6,820,897 B2 * | 11/2004 | Breed et al. | 280/735 |
| 6,923,545 B2 * | 8/2005 | Kitabayashi | 353/33 |
| 7,073,129 B1 * | 7/2006 | Robarts et al. | 715/740 |
| 7,145,661 B2 * | 12/2006 | Hitzenberger | 356/497 |

\* cited by examiner

*Primary Examiner*—Yosef Kassa
(74) *Attorney, Agent, or Firm*—Homer W. Faucett, III; Ice Miller LLP

(57) ABSTRACT

A portable, lightweight digital imaging device uses a slit scanning arrangement to obtain an image of the eye, in particular the retina. The scanning arrangement reduces the amount of target area illuminated at a time, thereby reducing the amount of unwanted light scatter and providing a higher contrast image. A detection arrangement receives the light remitted from the retinal plane and produces an image. The device is operable under battery power and ambient light conditions, such as outdoor or room lighting. The device is noncontact and does not require that the pupil of the eye be dilated with drops. The device can be used by personnel who do not have specialized training in the eye, such as emergency personnel, pediatricians, general practitioners, or volunteer or otherwise unskilled screening personnel. Images can be viewed in the device or transmitted to a remote location. The device can also be used to provide images of the anterior segment of the eye, or other small structures. Visible wavelength light is not required to produce images of most important structures in the retina, thereby increasing the comfort and safety of the device. Flexible and moderate cost confocal and fluorescent imaging, multiply scattered light images, and image sharpening are further functionalities possible with the device.

23 Claims, 9 Drawing Sheets

LASER SCANNING DIGITAL CAMERA WITH SIMPLIFIED OPTICS AND POTENTIAL FOR MULTIPLY SCATTERED LIGHT IMAGING

CROSS REFERENCE TO RELATED APPLICATION

The present application is a U.S. National Stage Application of International Patent Application Serial No. PCT/US07/12726, filed on May 30, 2007, the contents of which are herein incorporated by reference, which claims priority to U.S. Provisional Patent Application Ser. No. 60/809,551, filed on May 31, 2006, the contents of which are herein incorporated by reference.

STATEMENT REGARDING FEDERALLY SPONSORED RESEARCH

The work leading to the invention received support from the United States federal government under National Institutes of Health Grant No. EB002346. The federal government has certain rights in the invention.

BACKGROUND OF THE INVENTION

The human retina is susceptible to damage from a variety of environmental factors, including laser light impact and other trauma, as well as disease. Once damaged, the cells responsible for capturing light energy and transducing it into a neural signal, the photoreceptors, do not regenerate. In fact, none of the neural cells of the retina can yet be made to readily regenerate in the adult human. When damage is severe enough, there is permanent vision loss in an area. Healthy photoreceptors do not migrate long distances toward the damaged area to replace damaged ones.

If the affected region is in the central macula, known as the fovea, then the ability to see fine detail, read at rapid rates, or recognize objects at great distances may be lost. The peripheral areas of vision do not have sufficient sampling density to perform these tasks to the same degree. Thus, early detection and treatment of potentially sight-robbing damage are crucial in maintaining central vision.

One of the chief problems in early detection of damage has been the difficulty of imaging a small area of retina. The macula presents a small target—6000 microns. The portion that is necessary for seeing damage that precludes observation of fine detail and reading is even smaller, about 600 microns. To examine this latter portion properly, it is desirable to image the central 20 degrees of the macula with sufficient magnification and contrast to determine whether an individual is at risk for permanent vision loss.

The opthalmoscope or fundus camera has traditionally been used to view and image the retina. Originally, these devices flooded the retina with white light. Subsequent devices have used selective wavelengths that have been found suitable for viewing or imaging particular structures or contrast between structures. Regardless of the wavelength of light used, many of the past devices used flood illumination, producing images of the retina that often are subject to poor contrast due to long range scatter. The long range scatter problem was identified to occur, not only from out of plane tissues, but also from the biological tissues that are inherently scattering, especially those within and near the retina.

One well-known method of reducing the long range scatter problem is to replace a flood illumination source with a scanning illumination source. Some research has suggested that the use of a double scanning optical apparatus that scans both incident and reflected light using a horizontal scanning element may be desirable. Scanning with such an element can be performed by a rotating multifaceted polygonal reflector, and a vertical scanning element, such as a reflecting galvanometer. Such an instrument is able to provide a two-dimensional output representative of reflection characteristics of the eye fundus. See, e.g., U.S. Pat. Nos. 4,768,873 and 4,764,005, as well as U.S. Pat. No. 4,768,874 each disclosing a laser scanning opthalmoscope in which a line beam is scanned across an eye. Such improvements have greatly increased the contrast of the images produced, but typically require expensive, heavy equipment that must be operated by a specialist.

Improvements on the scanning illumination source technology have been embodied in the use of advanced reflectometry techniques with a scanning laser opthalmoscope ("SLO") as developed by the inventor, Ann Elsner, and colleagues. See, for example, Elsner A. E., et al., Reflectometry with a Scanning Laser Opthalmoscope, *Applied Optics*, Vol. 31, No. 19 (July 1992), pp. 3697-3710 (incorporated herein by reference). The SLO is advantageous for quantitative imaging in that a spot illumination is scanned in a raster pattern over the fundus, improving image contrast significantly over flood illumination. The inventor's SLO technology can further eliminate unwanted scattered light by using confocal apertures such as a circle of variable diameter or annular apertures, depending on the desired mode. Once the light is returned through the confocal aperture, the desired light can then be transmitted to a detector. However, the optics used in confocal apertures can increase the complexity of the system, and high quality optics are an added expense. Therefore, a method for reducing or eliminating unwanted scattered light in a more cost effective manner would be greatly appreciated.

Further improvements to increase contrast in retinal imaging systems include the extensive use of near infrared light as an illumination source, in lieu of other wavelengths or color images, as developed by the inventor and colleagues and described in Elsner, A. E., et al., Infrared Imaging of Subretinal Structures in the Human Ocular Fundus, *Vision Res.*, Vol. 36, No. 1 (1996), pp. 191-205; Elsner, A. E., et al., Multiply Scattered Light Tomography: Vertical Cavity Surface Emitting Laser Array Used for Imaging Subretinal Structures, *Lasers and Light in Opthalmology,* 1998; Hartnett, M. E. and Elsner, A. E., Characteristics of Exudative Age-related Macular Degeneration Determined In Vivo with Confocal and Indirect Infrared Imaging, *Opthalmology*, Vol. 103, No. 1 (January 1996), pp. 58-71; and Hartnett, M. E., et al., Deep Retinal Vascular Anomalous Complexes in Advanced Age-related Macular Degeneration, *Opthalmology*, Vol. 103, No. 12 (December 1996), pp. 2042-2053 (all of which are incorporated by reference herein). Combining infrared imaging with SLO allows the use of reflectometry techniques to view the eye rapidly and noninvasively because infrared light is absorbed less than visible light and scatters over longer distances. Further, when implemented with scanning laser devices, infrared and near infrared imaging of sub-retinal structure in the ocular fundus has been able to reveal sub-retinal deposits, the optic nerve head, retinal vessels, choroidal vessels, fluid accumulation, hyperpigmentation, atrophy, and breaks in Bruch's membrane—features that have proven difficult or impossible to observe with flood illumination devices. In addition, because infrared illumination is absorbed by the tissues less than other wavelengths, much less illumination from the source is required to create a high contrast image.

The improvements noted above, and methods for successfully imaging small retinal features were combined in U.S.

Patent Application No. 60/329,731; Ser. No. 10/493,044; 60/350,836; and PCT Application No. PCT/US02/32787, incorporated by reference herein. In addition, discussions of using the techniques for detecting and localizing such features are described in the publications of the inventor and colleagues: Elsner, A. E., et al., Infrared Imaging of Subretinal Structures in the Human Ocular Fundus, *Vision Res.*, Vol. 36, No. 1 (1996), pp. 191-205; Elsner, A. E., et al., Multiply Scattered Light Tomography: Vertical Cavity Surface Emitting Laser Array Used For Imaging Subretinal Structures, *Lasers and Light in Opthalmology*, (1998); Elsner, A. E., et al., Foveal Cone Photopigment Distribution: Small Alterations Associated with Macular Pigment Distribution, *Investigalive Opthalmology & Visual Science*, Vol. 39, No. 12 (November 1998), pp. 2394-2404; Hartnett, M. E. and Elsner, A. E., Characteristics of Exudative Age-related Macular Degeneration Determined In Vivo with Confocal and Indirect Infrared Imaging, *Opthalmology*, Vol. 103, No. 1 (January 1996), pp. 58-71; and Hartnett, M. E., et al., Deep Retinal Vascular Anomalous Complexes in Advanced Age-related Macular Degeneration, *Opthalmology*, Vol. 103, No. 12 (December 1996), pp. 2042-2053, incorporated by reference herein. The systems and techniques described in the inventor's previous patent applications introduced a moderately priced, portable system that provided a high contrast, digital image of the eye that could be used by non-specialists, such as paramedics or other individuals in the field. However, creating a system that is even less expensive, uses standard digital imaging technology, includes fewer high precision optics to obtain a high contrast image would be greatly appreciated in the art.

In addition, studies have shown that the multiply scattered light images, that are used to reveal structures in the deeper retina, can provide more detailed images that provide additional diagnostic utility. Further, the use of the infrared spectrum can be used to image the retina without dilation of the patient's pupils, and the added potential for using multiply scattered light, particularly in cases in which the target of interest falls below a highly reflective layer, allow visualization of features difficult to see otherwise. However, previous scanning devices, including those embodied in the patent applications submitted by the inventor and her colleagues, do not readily utilize this method for producing an image without scanning not only the light illuminating the target, but also scanning the light returning from the target to the detector, which requires considerable care. Therefore, a moderately priced, portable digital retinal imaging device that is capable of producing multiply scattered light images would be greatly appreciated in the art.

Existing devices specifically designed for screening of retinal disease that use flood illumination with bright lights of shorter wavelengths, and typically acquire single images at slow rates, have been shown recently to provide an unacceptable percentage of gradable images in the hands of technicians (Zimmer-Galler I, Zeimer R. Results of implementation of the DigiScope for diabetic retinopathy assessment in the primary care environment. Telemed J E Health. 2006 April; 12(2):89-98), regardless of the duration of training (Ahmed J, Ward T P, Bursell S E, Aiello L M, Cavallerano J D, Vigersky R A. The sensitivity and specificity of nonmydriatic digital stereoscopic retinal imaging in detecting diabetic retinopathy. Diabetes Care. 2006 October; 29(10):2205-9.) As discussed above, the embodiments of the present application address the issue of inconsistent use in the eye field. Other issues addressed by embodiments of the present application include onboard pre-processing of image and instrument parameter data for quality assurance and ease of use, addressing the issue of alignment of the instrument with respect to the target (e.g., small pupils and addressing and other issues regarding the anterior segment of the eye). The present application further addresses the prior art issue of failing to capture the images of the best existing quality, and failing to operate the instrument with optimal parameters.

Therefore, a moderate cost, portable retinal imaging device that provides for the use of a scanning laser device operating with near infrared illumination and which can allow for multiply scattered light would be appreciated in the art. Further, such a device that would allow for increased ease of use by allowing a greater field of view than just 20 deg visual angle, greater field of view without sacrificing spatial resolution, as well as utilizing a non-proprietary system for producing and saving the digital image, would be greatly appreciated.

SUMMARY OF THE INVENTION

The present application relates to a device designed as an improved digital retinal imaging device. In particular, the present application relates to a laser scanning digital camera ("LSDC") intended to be smaller and/or lower in cost than previous devices, while retaining a user-friendly format that allows a non-professional to obtain a high quality digital retinal image that can be easily stored, transmitted, or printed. In addition, according to another embodiment of the present application, the improved digital retinal imaging device may be used as a general imaging device or to improve image contrast in microscopy. Further, according to another embodiment of the present application, the additional aperture configurations and image processing capabilities provide a means for providing multiply scattered light images, which are useful for detecting structures that hidden under highly reflective tissue (e.g., deep retinal or choroidal disease underlying the vitreo-retinal interface and nerve fiber layer). In addition, according to certain embodiments of the present application, the device allows for increased illumination and/or light return at the edges of the field of view, thereby allowing for a more consistent, high contrast image to be produced. Finally, according to certain embodiments of the present application, a system and device allow for an increase in field size over previous embodiments, thereby allowing quality images to be taken even if the user is not adept at accurately aligning the imaging device with the eye.

Therefore, according to one aspect of the present application, the device is suitable for providing screening for eye diseases or triage for trauma and can readily interface with modern computer technology for remote or telemedicine applications. The device is able to operate in extreme heat or cold, when wet, while on a moving surface, and in a cordless, battery-powered mode. The device can be manufactured relatively inexpensively at significantly less cost than conventional scanning laser opthalmoscopes.

According to one embodiment of the present application, the device includes an illumination source, a scanning arrangement, a detection arrangement, a beam separation arrangement, and a controller. The scanning arrangement is disposed on an illumination path from the illumination source to a target and is operative to scan light passed through a slit in the illumination path across a desired focal plane of the target, e.g., the retinal plane, through an entrance more narrow than the desired focal plane, e.g., the pupil. The detection arrangement is disposed to receive light remitted from the target and operative to produce an image. The beam separation arrangement is disposed on a return path from the target separated from the illumination path and is operative to receive light remitted from the target and to direct remitted light on a detection path to the detection arrangement. The beam separation arrangement is configured to space the illumination path and the return path sufficiently apart to reduce reflections from sources out of the desired focal plane and sufficiently closely to obtain an image of a sufficient desired resolution. According to one embodiment, a controller is in communication with the illumination source, the scanning arrangement, and the detection arrangement.

In one embodiment, the device differs from previous instruments in that it features scanning of one or more light sources, one of which is preferably near infrared, at a much reduced cost. The device optionally includes on board digital memory or another storage device, such as is used in a digital camera. The instrument is stand-alone in one embodiment, and a personal computer is not required to operate the device. Further optionally, the data are transmitted to a computer, memory device, or other device including via wireless broadcast. A laptop and consumer grade software may be used to access the images if a computer is used. In addition, existing or large patient record systems, such as an electronic medical record system that can use image data are also a potential means of distribution or storage of data.

In one embodiment, the device is minimized in weight or mass and is portable, so that it is suitable for use outside of specialized opthalmological offices and laboratories. According to certain embodiments, the device can operate solely on batteries. The device of the present application is optionally motorized for remote access, using either DC operation or AC operation, as power supply permits. The device can be made to draw its power though a single cable, such as through a computer. The computer can be a laptop or personal data assistant, which is consistent with use as a portable device.

According to one embodiment of the present application, the digital imaging device is operable to provide a high contrast image by using an electronic aperture in the plane of the target or in a plane conjugate to the target, in either the input or detection pathway, or both. Optionally, the digital imaging device is further capable of providing multiply scattered light images by positioning the input and detection apertures in the plane of or near to the target, but offset with respect to each other. Alternatively, a multiply scattered light image may be obtained by positioning the input and detection apertures conjugate to the target, but offset with respect to each other, as described in further detail below. A multiply scattered light image provides diagnostic information not readily seen in the reflectance image, and may be accomplished by using a rolling shutter feature of a CMOS image array (discussed in further detail below) to sample an image line by line. This method leads to a high contrast image or a multiply scattered light image according to certain embodiments of the present application as discussed in further detail below.

The contrast of an image obtained through the method and/or device of the present application can provide details about structures such as retinal blood vessels that may be useful as screening or diagnostic data. Near-infrared illumination may be used to image the retinal blood vessels, thereby eliminating the need for short wavelength sources which require higher power and lead to pupil constriction unless medication is used to dilate the pupil. Therefore, the method and device of the present application provide a more comfortable experience for the patient, as well as a higher quality image that may prove more useful for diagnosis of diseases such as diabetic retinopathy and age-related macular degeneration. If more than one wavelength of illumination is used in the device of the present application, each wavelength can correspond to differing amounts of blood absorption, thereby allowing hemorrhages and other vascular features to be visualized in the comparison image.

DETAILED DESCRIPTION OF THE INVENTION

Figure 1:
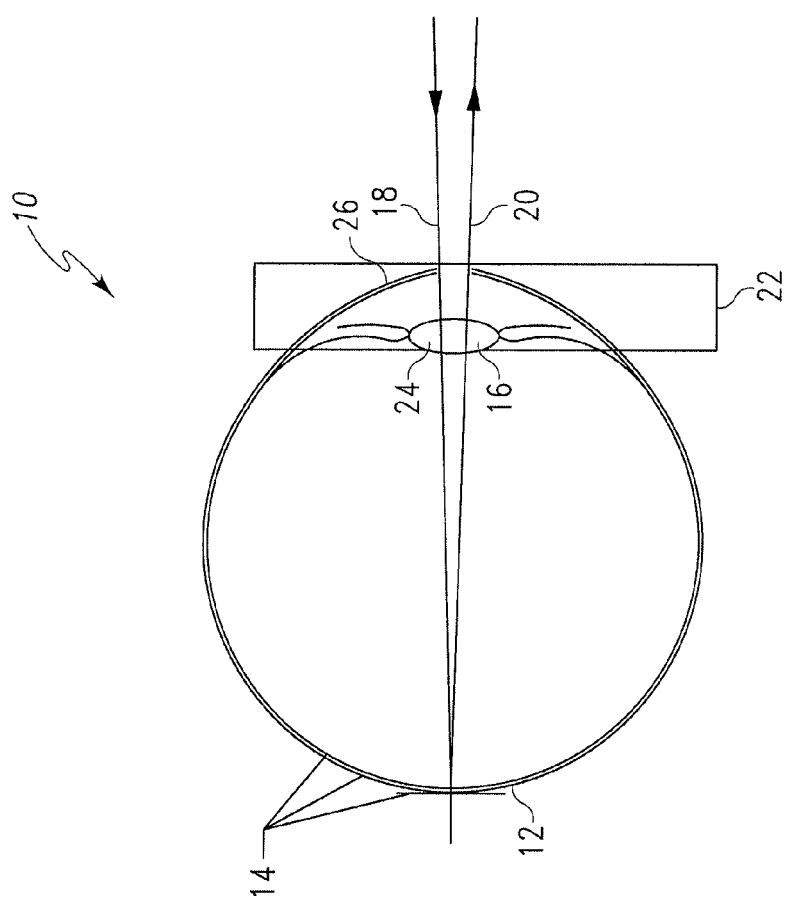
FIG. 1 is a schematic diagram of an eye showing selected tissues and the retinal plane as a target focal plane as distinguished from the highly reflective and more anterior optical planes.

The present application relates to a small, portable lightweight instrument or device of low cost particularly suitable for examining the retinal and subretinal layers of the eye 10 (see FIG. 1) for abnormalities. The device is noncontact and does not require drops to dilate the pupil of the eye in order to obtain a retinal or sub-retinal image. Referring to FIG. 1, the plane of focus 12 of the device includes the vitreoretinal interface and the retinal nerve fiber layer, which have the greatest amount of light return of the several sublayers of the retina 14. This area of greatest light return is helpful in finding the plane of focus, but presents a problem when trying to image through that area of the retina 14. When a human retina 14 is imaged, light from an illumination source is passed through a slit aperture to produce a line source and scanned across a desired focal plane in the eye after passing through the entrance pupil 16 of the eye. Light enters through one or more portions of the pupil (see exemplary illumination path 18) and is remitted and collected through other portions (see exemplary detection path 20), which minimizes the collection of unwanted light that is reflected from other planes 22, such as the lens 24 and cornea 26, that would be on the same optical axis if the illumination and detection pathways were coincident. Slit scanning of the illumination onto the target, discussed further below, reduces the amount of target area illuminated at a time, thereby reducing the amount of unwanted scatter from both nearby and distant structures, which are not illuminated simultaneously with the light illuminated by the slit, thereby providing a higher contrast image.

According to one embodiment, the light from the desired focal plane is collected and stored digitally in electronic or magnetic form and/or transmitted to a remote site if needed. The footprint of the optical components can be minimized and the device is optionally operable by DC battery power. Optionally, the main controls are few and simple, primarily a power switch, a focusing mechanism, a mechanism to increase or decrease the light level of the illumination source that may be under operator control or automatic, a mechanism to initiate acquisition of images, and a mechanism to control the storage or transferal of the images.

Figure 2:
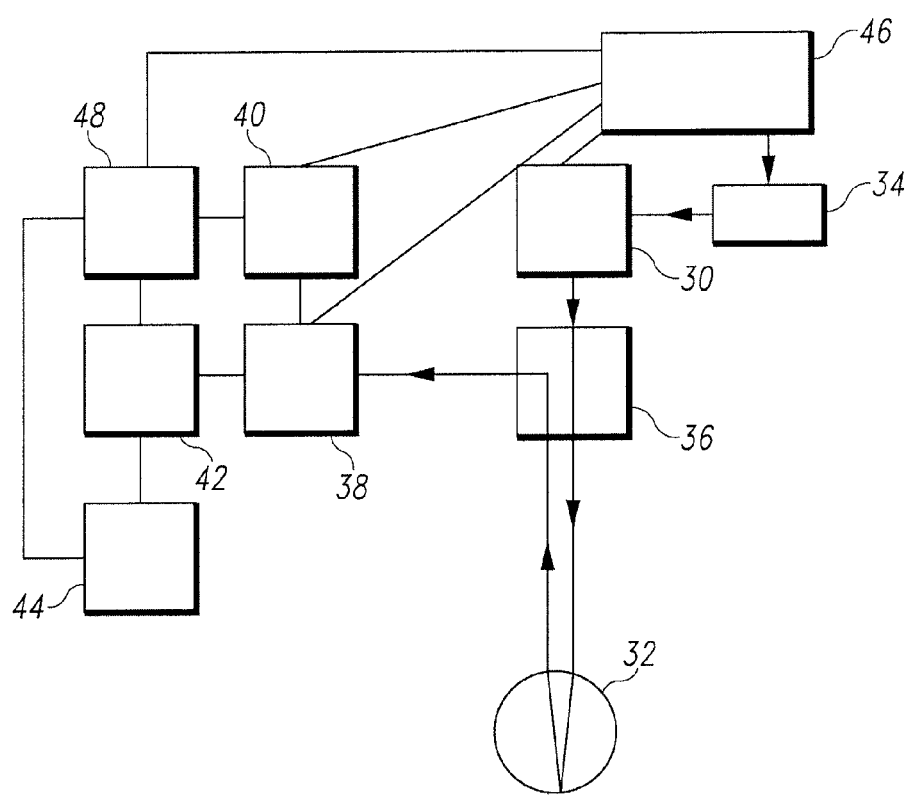
FIG. 2 is a schematic diagram of a prior art optical imaging system, and upon which the present application is an improvement thereof.

FIG. 2 depicts generally an optical imaging system according to the present application. One or more scanning elements 30 direct the light to and, in some embodiments, from a target 32 to decrease the unwanted scattered light that would result with flood illumination. This system includes an illumination source and beam shaping optics, illustrated collectively at 34, for directing incident light at the scanning element 30, which then directs the light through a beam separation element 36, then at the target 32. The intended target for the present device is within the eye, although the device can be used with other targets. An illuminated portion on the target 32 remits light via a beam separation element 36 to components along a detection pathway, illustrated schematically at 38, where an image of the target is formed, and light energy is changed to electrical or magnetic energy, for purposes of image capture or image storage. The collected image is then shown on a display 40 and/or stored on a storage device 42 in communication with the components on the detection pathway 38. The image can additionally or alternatively be transmitted either by storage media, cables, or wireless communication to a database 48 or to a display, computer, personal digital assistant, or other digital or analog device 44 for the purposes of examining the target 32.

Control electronics or mechanical adjustments, illustrated schematically at 46, allow the end user or an automatic process to control the illumination source 34, the scanning element 30, the detection pathway components 38, the display 40, and the database 48, as well as devices such as alignment or focusing monitors, synchronization circuitry, transmission using wires or wireless methods, additional image monitors, image capture or recording devices, and image storage devices that are interconnected with them. These resulting images can be fed into the database of image data 48, or used without reference to the database. The database of images 48 may be used via components 44 for telemedicine, training, and distance education concerning the status or health of the target, as the user of this instrument may be remote from a decision maker or may be unskilled in the arts of image acquisition or image interpretation of this type of image. The database can also contain normative, classification, or quantitative data and decision-making procedures concerning the outcome of the data.

The separation element 36 can be any type of separation element, such as a beam splitter with the reflective portion intersecting the beam of light and directing it towards target 32, while the more transmissive portion passes the light toward the detection pathway 38, shown schematically in FIG. 2. The beam separator can also work such that the transmissive portion intersects the beam of light directed towards the target, but reflects the light returning from the target. A beam separator that permits only a minimal amount of spatial overlap between the light directed towards the target 32 and the light remitted from the target, and similarly the entrance pupil to the target, provides the benefit of minimizing the collection of light from reflective surfaces that are not in the plane of the target. When the human eye is the target 32, the light enters in one or more portions of the pupil of the eye, and is remitted and collected from primarily other portions of the pupil, as discussed above in conjunction with FIG. 1. The beam separator 36 can have one or more reflective or transmissive portions. These reflective and transmissive portions can be made of reflectors of a relatively permanent nature, or can be made of elements that separate the beams by means of polarization properties of the light directed towards and away from the target. With a mirror beam splitter, the light entering the eye can have the greater loss of transmission through the beam splitter, to preserve more of the light returning from the eye. The beam separator can be controlled by known electro-optic devices such as liquid crystal display ("LCD"), spatial light modulator, or polarizing elements. With a polarizing beam splitter, additional polarization elements can be used to reduce unwanted reflections from the anterior segment. The beam separator can use elements positioned mechanically, thereby controlling the position or amount of the light towards or away from the target. The beam separator can contain reflective or transmissive elements that are only partially reflective, such as a 90/10 beam splitter. When the target is the human eye, the preferred embodiment includes a separation element that can make use of a small and powerful illumination source 34, with a relatively lesser return from the eye.

Figure 3:
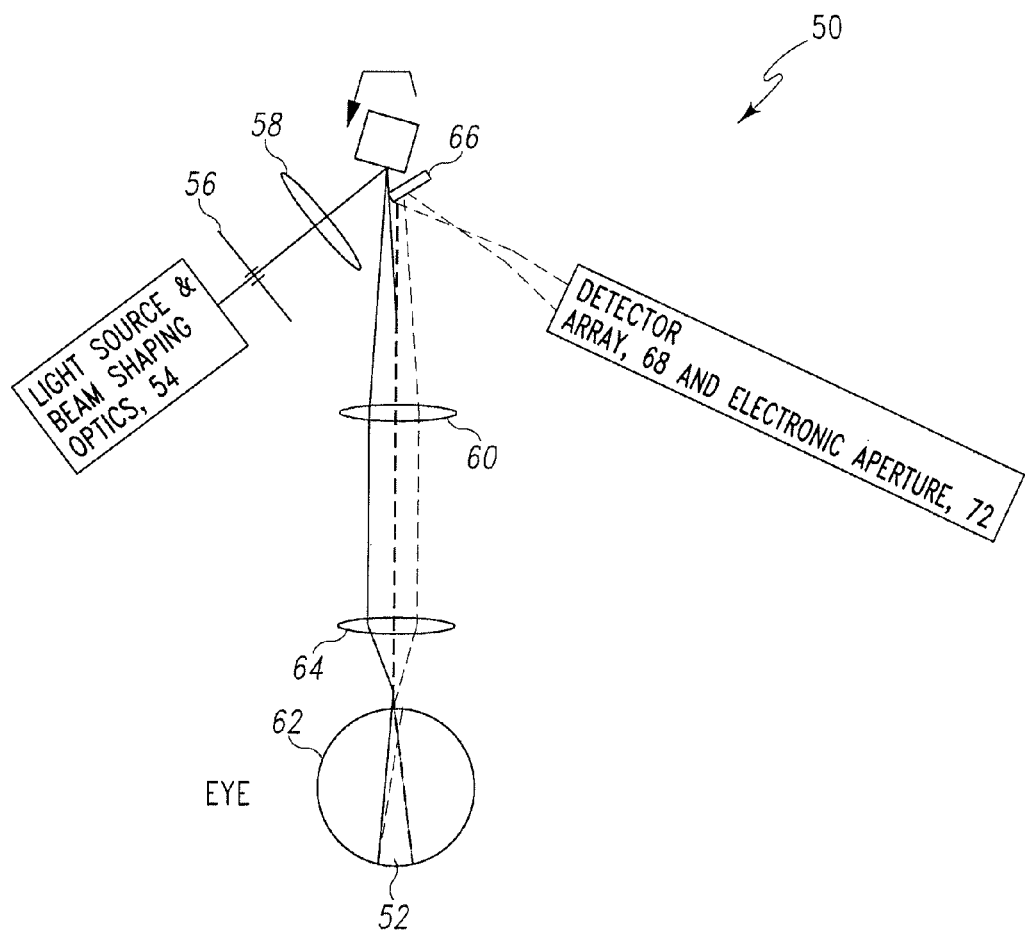
FIG. 3 is a schematic diagram illustrating an embodiment of the optical imaging system of the present invention incorporating one scanning element.

FIG. 3 illustrates an embodiment, which describes a group of configurations, in which a single scanning element 50 directs light from a light source and shaping optics 54 to a target 52 but not the light remitted from the target 52. The light from an illumination source 54 undergoes beam shaping and is brought to a focus in a plane conjugate with the target 52 at a slit aperture 56. According to one configuration, illumination from an illumination source 54 utilizes beam shaping optics well known in the art that change illumination from quasi-Gaussian to a slit output. This change in illumination may be accomplished by using a cylindrical lens in the illumination pathway prior to the slit 56. However, if edge emitting illumination devices or other linear devices are used, a cylindrical lens may prove unnecessary. Slit aperture 56 is illustrated in more detail in FIGS. 5-8, and further described below. As can be seen in FIG. 3 and FIG. 9, slit 56 has a long axis orthogonal to the plane of the figure.

In FIG. 3, the light passing through slit aperture 56 is directed by a focusing element 58 onto the scanning element 50. The scanning element 50 rotates or oscillates to reflect the light sequentially across the target in a direction perpendicular to the long axis of slit aperture 56. Throughout the figures, solid lines exiting the scanning element 50 indicate a scan path for the illumination, and broken or dashed lines indicate detection pathways. From the scanning element 50, the light is then directed by one or more focusing elements 60, through a narrow angle of entrance, (e.g., the pupil) 62, to a focus at the target 52 (e.g., the retinal plane). FIG. 3 illustrates the entrance and focal planes schematically only; see FIG. 1 for greater detail. The light at slit aperture 56 is in an optical plane conjugate to the target 52. The light at scanning element 50 is in an optical plane conjugate with the plane of the narrow angle of entrance 62. A focusing element 64 is preferably mounted for movement in an axial direction to allow focusing of the light on the target 52. When imaging a target without a lens (e.g. a target other than the human eye with a functional lens), focusing element 64 is optionally a set of lenses suitable for focusing on the target 52.

As noted above, scanning the light across the target through a slit aperture (and scanning again in the detection pathway if this is performed, described further below) aids in decreasing unwanted scattered light in the resulting image. The scanning can be accomplished in a variety of ways well-known in the art. For example, a mirror component may be mounted to a rotating or oscillating element, a magnetic device, a spring, a torsion rod, or other mechanically controlled device such as a solenoid, or a gravity controlled device. The scanning element can be activated in any suitable manner, such as by a button or lever press, a sliding switch, a toggle switch, or a knob rotation by the operator. In one embodiment, the scanning element is preferably driven by a battery operated DC motor, which is an inexpensive configuration and allows the device to be portable. In one embodiment, a rotating element that rotates in one direction, such as a DC motor may be used. Such a motor may be selected to be quiet in operation and operate with little disruption from environmental vibrating.

Light returning from the target 52 is separated from light striking the target at beam separation element 66. In the embodiment shown in FIG. 3, separation element 66 is illustrated as a mirror that does not intersect the light directed towards the target 52 on the illumination pathway. The mirror is located on the return pathway to intersect and thereby reflect the light remitted from the target 52 on the detection pathway to a detector array 68. The separation element 66 may also comprise a beam splitter with the reflective portion intersecting the beam of light directed at the target 52, with the transmissive portion directing light remitted from the target, or any other combination of elements as described concerning FIG. 2 above to separate the light from the illumination pathway from that remitted from the target 52 and direct the remitted light towards the detection pathway. Separation element 66 optionally contains additional mirror surfaces to direct the light in a direction convenient with respect to the configuration of the other components, thereby allowing crowding of components near the target 52 to be reduced. Further, additional mirror surfaces may be used and configured to reduce component crowding near mounting surfaces of focusing elements 60 and 64, or to prevent components from interfering with the motion of either focusing element 64 or scanning element 50 by spatially separating the light directed towards the target 52 from the light returning from the target, unwanted, direct reflections from focal planes not in the plane of the target can be eliminated by minimizing the spatial overlap at beam separator 66. With respect to the target, the illumination is directed at the target from a slightly different position than is the detection pathway from the remitted light so that there is minimal spatial overlap between the detection and illumination pathways, thereby minimizing any unwanted reflections of optical elements, including those often found in association with the target such as the cornea and lens of the human eye when the retina is the target (see FIG. 1).

The separation element 66 may comprise a partially or fully reflective surface that does not intersect the light directed towards the target 52. The reflective surface may comprise a mirror or a beam splitter with the reflective portion not intersecting the beam of light directed at the target, as shown. The separation element can also be any number of other separation elements, such as a beam splitter with a reflective portion intersecting the beam of light directed towards target and a transmissive portion including a mirror that reflects less than 100% of the light towards the target or a transmissive portion intersecting the beam of light directed towards the target and the reflective portion allowing the light from the target to pass.

According to one embodiment of the present application, further decrease of light from unwanted planes can be obtained by directing the light on the detection pathway from the target 52 to a two-dimensional detector array 68 comprising a complementary metal-oxide-semiconductor chip ("CMOS") (referred to as a "CMOS detector array"). The CMOS detector array operates in such a way that it acts as a "rolling shutter" because an image is formed by digitizing in an iterative line-by line fashion. Thus, as a beam of light is directed onto the CMOS detector array, only one small line or region of the image is read or exposed at any given time. Therefore, only light in phase with the particular line being read or exposed by the CMOS detector array is collected by the CMOS, thereby causing the digital image of the target to be "built" one line at a time. Optionally, if a more advanced CMOS detector can be used, allowing more than one line can be built simultaneously, and providing additional benefits and functionality discussed more thoroughly below. The use of the CMOS in lieu of a charge coupled device chip ("CCD chip") as used in previous embodiments creates multiple unexpected benefits. While it was previously thought that synchronizing the rolling shutter feature of the CMOS detector array with the scanning slit aperture would be difficult, thereby increasing costs in production of the device, it has been found that use of the CMOS detector array itself acts as a confocal aperture due to its rolling shutter function, thereby eliminating the need for several expensive focusing and other elements that were necessary in the detection pathway in earlier embodiments. In addition, it was found that the use of the CMOS detector with a rolling shutter feature significantly reduces or eliminates blooming of an image, and further allows several additional functionalities to be present in the device that were not present in previous embodiments. According to another embodiment of the present application, an optional electronic input aperture is substituted or added to allow adjustment of the width of the slit that is scanned, as well as the width of the slit that is detected through the detection pathway.

In addition, the use of a CMOS detector array allows one to eliminate elements between beam separator 66 and detector array 68. This allows for a complete change of the geometry of the device, because the rolling shutter feature reduces the need for a third scanning face and facets needed during the acquisition of each image. The elimination of these components allows for a reduction in optical aberrations that affect the resultant image, and further allow for an increased field size imaged by the device. For example, the present embodiment allows for a field of view 1.5 to 2 times wider than the twenty degree (20°) field size of the previous embodiments without otherwise significantly altering the design of the device. A greater field of view of the device translates into a more user friendly imaging system, because an operator does not need to align the device with the eye as exactly as he or she would be required with a device that was more limited in field size.

Yet another functionality achieved through the use of a CMOS detector array with a rolling shutter feature is the ability to use scattered light imaging, increased sampling in the case of low signal, and image sharpening. For example, if the CMOS array is read line by line, it is possible to select a leading line or a lagging line in precise alignment with the optical axis of the illumination beam. When the illumination beam is digitally imaged, using the leading or lagging line or both together, a scattered image results. In one embodiment, two or more lines are digitally imaged in close succession to one another, or even simultaneously. Imaging these two or more lines allows for an overall image with a more precise image of a moving target, such as an eye, and allows reduction or elimination of shadowing from detection that is asymmetric. With non-moving targets, two images are acquired sequentially and then combined to provide a multiply scattered image without the use of advanced CMOS hardware. In addition, the input and detection apertures can be adjusted relative to each other to provide increased illumination control, more or less scattered light, and correction of poor illumination or return at the edges of the field. An electronic shutter can operate with sufficient speed to alter the illumination pathway within each line of the image when necessary as discussed further below. Optionally, more than one line in the CMOS detector can be activated to allow the detection of more light, with or without the additional aperture.

Using the imaging method described above, one embodiment of the present application allows for image sharpening when two or more lines adjacent to the on-axis line on the CMOS output are subtracted from the on axis line. Optionally, the two lines may be subtracted in a weighted manner. While it has been known in the art to use image processing with high contrast laser images to create such image sharpening, the image processing has always been done after the image was created. The present embodiment of the device allows the sharpening and image processing to occur while the target is being imaged, thereby allowing the operator to see the sharpened image at the time the target is in front of him or her. Therefore, since the sharpened image is able to be viewed by the operator while taking the image, the operator can determine whether additional images need to be taken to ensure that a quality image results.

According to yet another embodiment of the present application, a bi-directional scan is utilized, wherein multiple lines are detected and imaged sequentially (or otherwise) in differing directions. For example, a first scan sequentially detects and images lines toward the left of the starting position while a second scan sequentially detects and images lines toward the right of the starting position. Optionally, both the first and the second scan occurs simultaneously, and timing software is used to create multiply scattered light images from these scans.

Utilizing a CMOS detector array 68 to detect and build an image has the additional advantage over previous embodiments in that images obtained with a device according to the present application are optionally stored to memory media that is common—even in the retail consumer market. For example, experiments utilizing certain embodiments of the present application utilized flash memory cards and digital capture cards in a typical personal computer processor or digital camera. It will be appreciated that several other conventional or non-conventional storage media well known in the art may be used to acquire images detected by the CMOS detector array. Yet another advantage to using a CMOS detector array in lieu of a CCD chip is that the CCD vertical resolution is decreased by a factor of 2 in each field, because the CMOS detector array is not interlaced as is the case with interlaced CCD chips. Progressive scan chips do not have the reduction of vertical resolution, and along with CMOS chips are preferred when target motion such as eye movements are of concern because sequential scanning and similar schemes allow an image to be built up with adjacent structures sampled at more similar points in time, compared with interlaced schemes that acquire odd lines, and then even lines. Additionally, interlaced CCD chips require a 30 Hz frame rate, whereas CMOS chips operate at a lower sampling rate, thereby allowing improvement of signal to noise ratio. Further, use of a CMOS detector array instead of a CCD chip has resulted in reduction of stray light from the several reflective surfaces required in the CCD embodiments, including those that allow the collection of light before and after the time period contributing to the image, with the CMOS embodiment thereby increasing detection of a higher proportion of light related to the target and improving image quality over sample and hold systems.

Returning now to FIG. 3, in cases in which a CMOS with a rolling shutter serves as the two dimensional ("2D") detector array 68, the reading of the data line-by-line in a sequential manner serves as an aperture 72 to limit the unwanted stray light. Only the light striking the line being read contributes to the image, which is in a manner analogous to only the light passing through a slit aperture reaching the target. As the CMOS chip is in a plane conjugate to the retinal plane, use of its inherent sampling scheme constitutes a confocal aperture, thereby reducing optical crosstalk spatially and increasing image contrast.

In cases in which the 2D detector array 68 has a sample and hold or other strategy that does not include timed line-by-line sampling to limit the area sampled at a given time, then a separate electronic aperture may be introduced to serve as detection pathway aperture 72 shown in FIG. 4. An LCD array that is pixel-by-pixel or line-by-line addressable and changes from transparent to opaque may be placed in close proximity so that the light in the detection pathway is limited spatially, and the area that is transparent corresponds to that being illuminated by the scan across the 2D array 68. As the scan progresses, the transparent area sweeps along in corresponding manner. However, this method requires another element to control for timing the sweeping action of the transparent area, unlike the CMOS rolling shutter method. According to one embodiment, a separation element 66 may be used to reduce pupil plane, or non-conjugate plane, reflections significantly. For targets that are stationary, or targets that can tolerate more light and thus could be scanned with high intensity and high speed, this objective may be removed.

For purposes of microscopy or fluorescence measurements in the eye, the electronic detection pathway 72 may optionally be made so narrow as to allow optical sectioning or wide enough to incorporate as much signal as possible, and may be configured as to include or exclude fluorescent barrier filters.

The rotation of scanning element 50 shown in FIG. 3 is in sufficient synchrony to allow line-by-line correlation of the illumination beam as it is scanned. Therefore, the position of the of aperture 72 is reasonably synchronized with scanning element 50. This may be accomplished either via open loop and calibration or closed loop methods well known in the art.

Figure 4A:
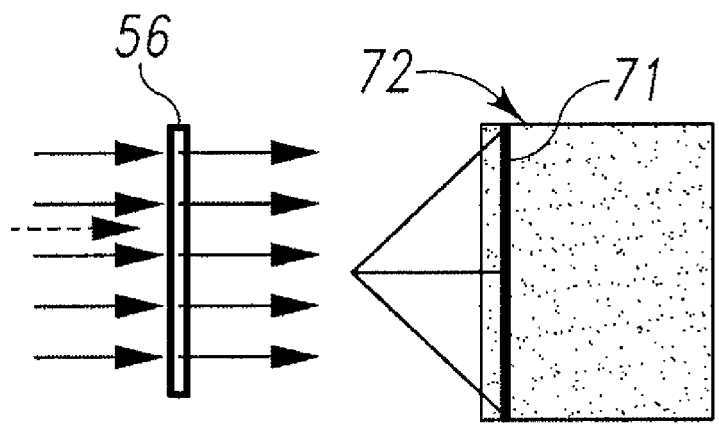
FIGS. 4a and 4b are schematic diagrams illustrating an embodiment of a slit aperture used in the illumination pathway, and further illustrating the use of a CMOS detector array utilizing a rolling shutter function to operate as an aperture in the detection pathway to limit sampling prior to the detector such that light primarily in the plane of focus of a target in a conjugate optical plane.
Figure 4B:
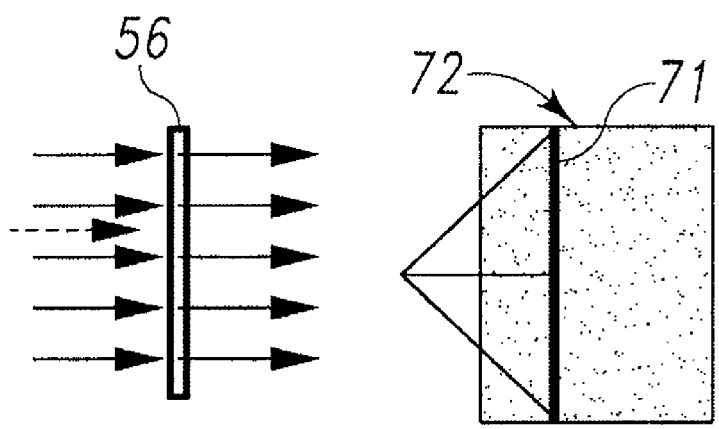

FIGS. 4a and 4b further demonstrate a certain embodiment of the slit aperture 56 conjugate to the retinal plane in the illumination pathway and the electronic aperture conjugate to the retinal plane in the detection pathway. As shown in FIG. 4a, at a first time, light passes through slit 56, travels through the instrument, and the linear beam of light 71 is swept across the electronic aperture 72. As shown in FIG. 4b, at a second time equal to the first time plus an additional time, the linear beam of light 71 has moved to a second position on electronic aperture. Unwanted light from planes outside the target area, as well as light that has scattered across the target, is reduced by the use of aperture 72. As stated above, the rolling shutter function of the CMOS chip has this property inherent in its operation. Alternatively, according to another embodiment of the present application, a mechanical, electronic, or other shutter with a movable transparent area may be used in close proximity to the 2D detector array, allowing another 2D detector array such as a CCD, video camera, or other detector array to be used. The transparent area may be readily moved in devices such as LDC displays.

Figure 5A:
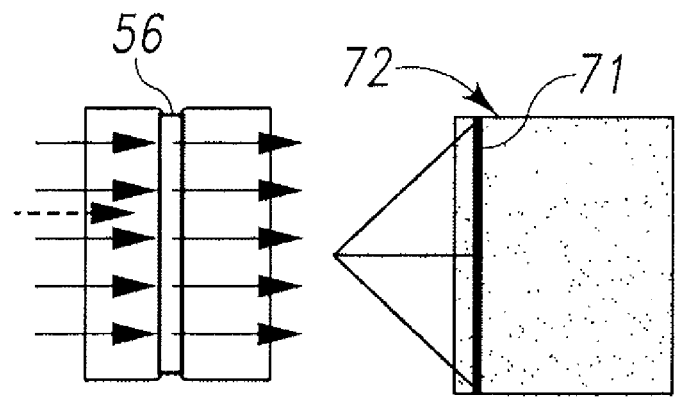
FIGS. 5a and 5b are schematic diagrams illustrating an embodiment of a slit aperture in the illumination pathway to control intensity of the illumination light, and also illustrating a CMOS detector array utilizing a rolling shutter function to operate as an aperture in the detection pathway to limit sampling prior to the detector to light primarily in the plane of focus of a target in a conjugate optical plane.
Figure 5B:
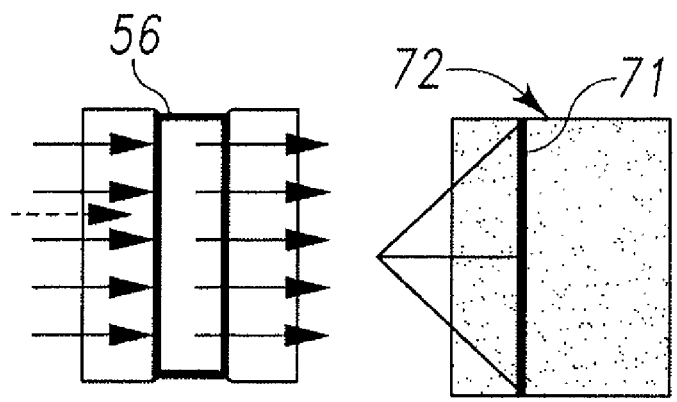

FIGS. 5a and 5b illustrate that the width of slit 56 may be adjusted readily, and in a more rapid manner when it is electronic than when it is mechanical. As shown in FIG. 5b, a wider slit allows more light to enter the imaging system, thereby increasing image intensity. The relative widths of slit 56 and detection pathway 72 determine the sampled region, and increase or decrease the depth of field. Very narrow elements in slit 56 and detection pathway aperture 72 lead to a small volume of light sampled at the detector, and therefore optical sectioning and high contrast in the plane of focus, as shown in FIG. 5a. Wider elements, such as that depicted in FIG. 5b, allow a large volume of light to be sampled and a larger depth of field more readily useful in the moving eye. More scattered light is collected in the configuration shown in FIG. 5b, and this scattered light information can be useful in revealing structures not otherwise seen.

Figure 6:
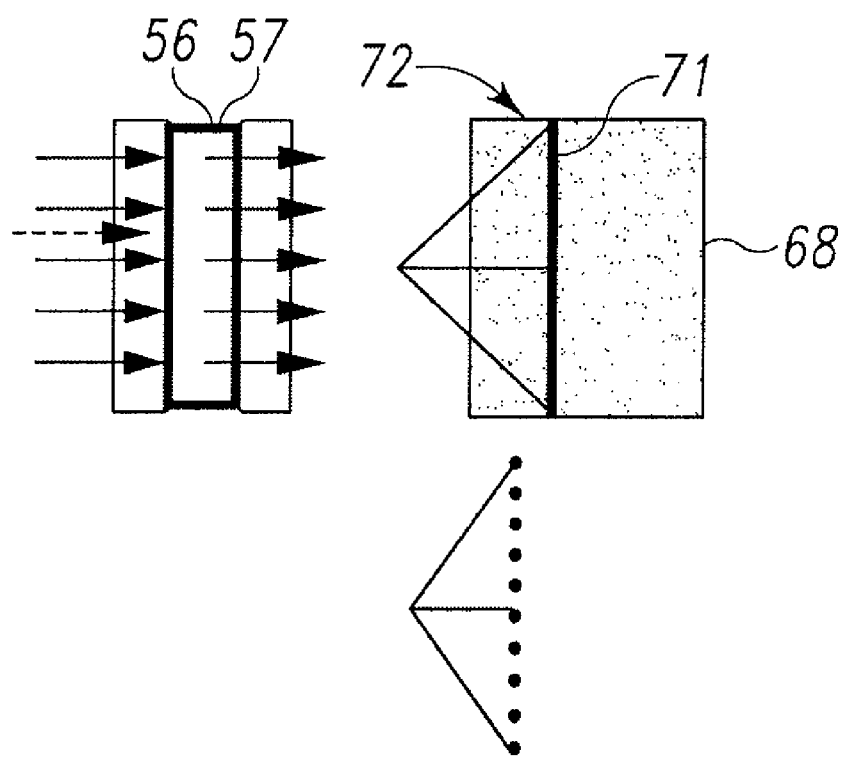
FIG. 6 is a schematic diagram illustrating an embodiment of the optical imaging system of the present application incorporating one scanning element and an electronic input aperture as a slit aperture, and also illustrating a rolling shutter function as an aperture provided by electronic means in the detection pathway to alter sampling.

FIG. 6. depicts a method for producing scattered light imaging with a relatively wide slit 56 in the illumination pathway made by any means that transmits light such that a wider area of the target is illuminated and the light returning is captured by a confocal aperture in the detection pathway 72 that is offset from the main illumination axis, shown by the dashed lines beneath detection pathway aperture 72. Detection pathway aperture 72 acts as an electronic aperture that is inherent in the CMOS shutter. Specifically, detection pathway aperture 72 acts as an electronic aperture by assigning a column on the chip to actively obtain image data that are advanced or delayed from the main illumination position on the target. The position(s) and width(s) are readily modified with ancillary electronic apertures, but, in the rolling shutter (line-by-line read out) on a CMOS chip, there must be onboard processing or post-processing to incorporate any functions other than a delay or advance of image capture via the synchronization. This method produces multiply scattered light imaging, but results in asymmetric illumination and detection, which can lead to shadows in the image that are difficult to distinguish from absorptive structures. Symmetric illumination can be obtained by combining two images, each having a displaced read-out from the illumination, but in opposite directions from the illumination axis. This is not a disadvantage with nonmoving targets when relatively high light levels are used, and when two images may be taken is close succession. However, when moving targets are imaged, an alternative embodiment utilizes two detector arrays (such as CMOS detectors) simultaneously, with independent shutters, with one detector array allowed to lead the light source, and the other lagging behind.

Figure 7:
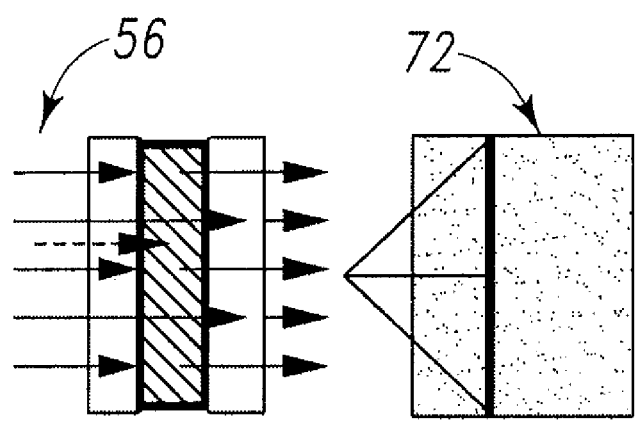
FIG. 7 is a schematic of a combination of input and detection pathway apertures to provide confocal imaging, multiply scattered light imaging by means of off axis illumination, multiply scattered light imaging by means of two or more off axis detection, by utilizing two or more off axis detection components.

Turning now to FIG. 7, according to yet another embodiment of the present application, another method for producing scattered light imaging utilizes a patterned input illumination by introducing two or more transparent regions to the slit 56 in the illumination pathway and using the detection pathway aperture 72 as a confocal aperture. In this example, the central or on-axis portion of slit 56 is opaque and two transparent bars flanking the central portion of that slit. Light transmitted off axis is led through the instrument to the target, and the portion that returns on axis passes through the detection pathway aperture 72, which is on axis. The on axis light returning from the target is largely scattered multiple times off target structures, and that light that is singly scattered from the illumination pathway slits 56 is blocked by the aperture. With an electronic aperture, this light arrives at the wrong time to pass through the aperture or be sampled by the rolling shutter action of CMOS chip 68.

Figure 8:
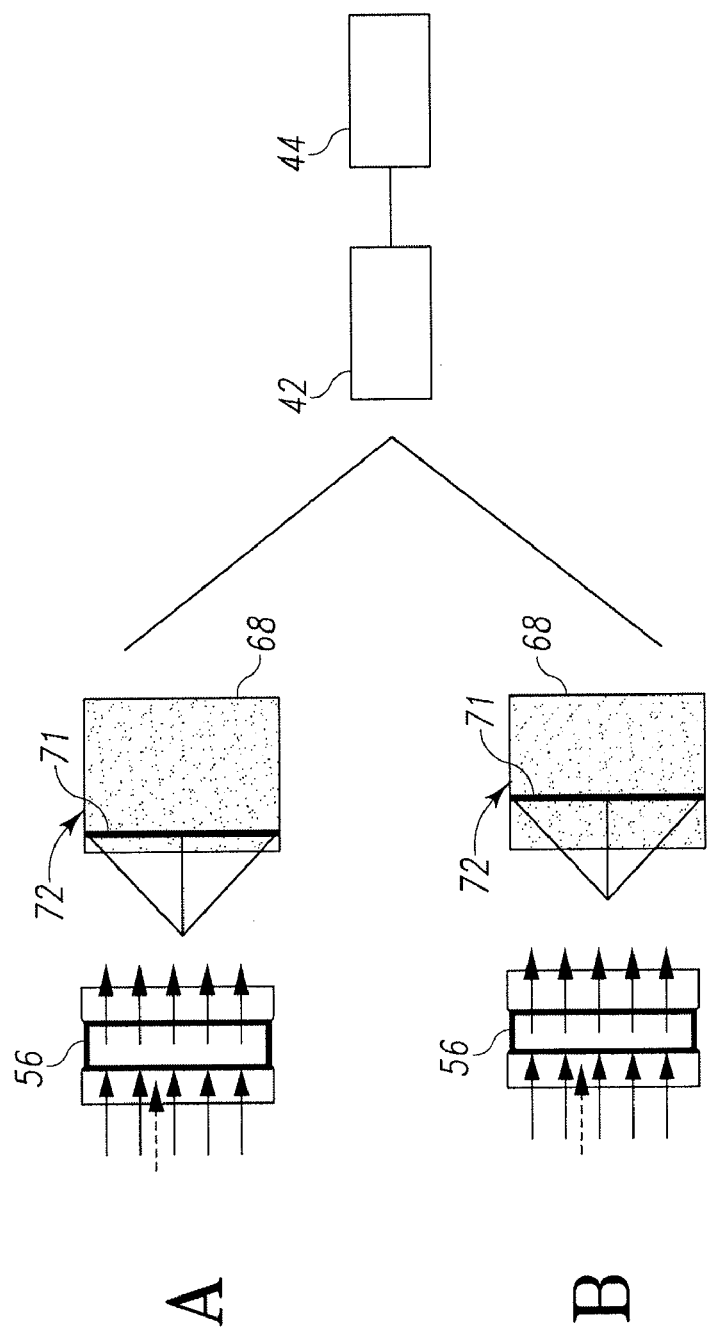
FIG. 8 is a schematic showing the combination of input and detection pathway apertures along with processing to provide confocal imaging, image sharpening, and multiply scattered light imaging.
Figure 9:
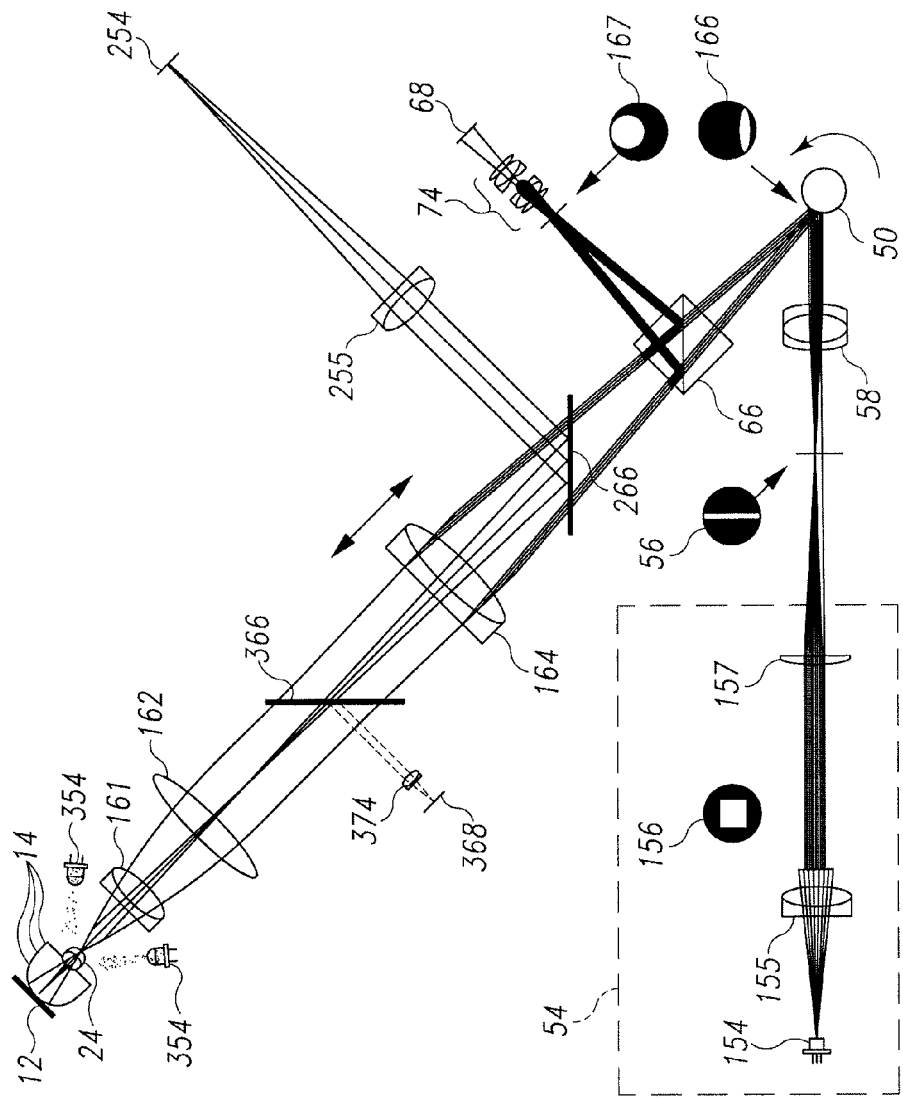
FIG. 9 is a detailed drawing showing one configuration of a roughly 40 deg field of view digital imaging device.

FIG. 8 illustrates sample combinations of slit 56 and aperture 72 with post processing to achieve confocal imaging, multiply scattered light imaging, and/or image sharpening. Processing may be accomplished by using either a detector array 68 with onboard processing, or digital or analog device(s) 42 for storage and comparison of the images, thereby allowing image comparison or computation. For example, as shown in FIG. 8, a multiply scattered light image is taken with the linear beam of light 71 taken at time A (referred to as "line A"), and linear beam of light 71 taken at time B (referred to as "line B"). Time A and B may be the same time, may be sequential, or may be at significant periods of time apart from one another. As an example, the scanning occurs progressively, with sampled lines A and B, and, illustratively there may be an additional line C (not shown), such that line B is between line A and line C on the detector array 68. By using the simple formula aB−b(A+C), where a and b are the weighting factors with variable sign and amplitude. To accomplish highly flexible confocal imaging, a is positive and b is negative and between 0 and 1, then a portion of the light received through A and C will be added to the light from B to form an image, with A, B, C, and any further lines together serving as a confocal aperture of adjustable width and with the possibility to capture a variable portion of the scattered light not passing through B, optimized according to imaging task. To accomplish image sharpening, if a is positive and b is positive but between 0 and 1, then this formula is used to subtract a portion ranging from 0 to 100% of the amount of light in A+C, thereby removing the scattered light from an image based on B without further need for adjustment of slit 56, accomplishing image sharpening. Optionally, this method may be generalized to more lines than A through C, and additional weighting factors, allowing the full flexibility needed for each imaging task. For multiply scattered light imaging, weighting factor a is negative or a factor less than 1, and b is negative, so that more total weight is assigned to data passing through lines A and C. Again, additional lines, including those lines further removed from B, and corresponding weighting factors may be used to provide flexible imaging according to the target and imaging task. For weak multiply scattered light signals, proportionally more weight may be needed to be given to achieve an image.

The quality of the beam in imaging is important, and a slit can be formed by using only a cylindrical lens in beam shaping portion of element 54 and by slit 56 in FIG. 3, but using both elements improves energy efficiency via element 54 and the slit 56 allows for more precise sampling than does using only by element 54. Optionally, light at the slit 56 is in an optical plane conjugate to the plane of the target 52. Further, optionally, the slit can be generated by a transmissive or reflective spatial filter, as well as an electronic one, such as a spatial light modulator or LDC device, as described above. Additionally, the beam quality and slit may be optimized for a specific imaging task.

The position of the target plane is manipulated by the movable lenses or other focusing elements, for instance lens 64 shown in FIG. 3. In one exemplary embodiment, the dimensions of the input pupil to the target 52 are small, no more than 2.5 mm in diameter. This permits use of the device in brightly illuminated surroundings or with older people in a remote setting. The size of the target to be imaged, when the human eye is the target, is from about 6 mm to about 12 mm, differing from highly magnified experimental instruments, but providing a field of view of about 20° to about 40° visual angle as in conventional ophthalmic cameras.

As the input and exit pupils are limited to a total of about 2 mm to about 2.5 mm, light efficiency is a concern, particularly when the pupil is not dilated. According to one embodiment of the present application, scanning is done in one dimension unlike the majority of commercial devices, which scan in two dimensions. An improvement in signal to noise ratio can be achieved by reducing the speed of scanning. Unlike prior art commercial devices, which do not scan, an improvement in light efficiency may be obtained and an improved image quality is obtained by scanning.

A criterion in the design of a device according to the present application is to preserve a substantial amount of light, thereby allowing a maximum amount of light to reach the detector from the eye. Using such a criterion in design allows significantly better imaging, particularly since retinal imaging according to the present application is often performed through a pupil that is not dilated—thereby creating a condition that would be considered to be "light-starved" in other systems. In addition, the scanning device can operate slowly near the range of about 1 HZ to about 30 Hz, rather than the typical devices used for retinal imaging such as a continuously moving galvonometer or rotating device that operates at about 25 Hz to about 60 Hz. The lower frequency range also allows for less power consumption and a mechanically less sophisticated device to be used for scanning. The slow scan can be done such that, when the scanning device is activated by the operator, the scanning can be done with a single or limited number of sweeps across the target.

While the foregoing describes several embodiments of a device according to the present application, it will be appreciated that several other considerations may be taken to alter the application of the device, or to alter configurations of the device. For example, in another embodiment using a limited number of scans, reduced resolution is used during one or more frames to assist with light level, target positioning, and focusing faster data acquisition, and then higher resolution is used for one or more good quality still frames. Many two dimensional arrays used in consumer electronics now permit operation in more than one mode. Similarly, detector arrays offer more than one resolution. Thus, scanning and acquisition speed, light level, and gain can be traded off against resolution, as will be appreciated by those skilled in the art.

It will be appreciated by those in the art that the small pupil size and small device size impose constraints on the field of view, which is most likely to be approximately about 20° to about 40° with optical resolution that supports a digital resolution of approximately 512 pixels×512 pixels or 640 pixels× 480 pixels up to a 1 megapixel detector. A large depth of field is preferred for use with human patients, and the device may have intentionally limited confocal sectioning capabilities. A large depth of field reduces the need for a large input beam at the pupil, which allows for better axial resolution. Reduction of out of focus light minimizes artifact from anterior segment optics. An aperture in the plane confocal to the retinal plane is optionally used according to one aspect of the present application. Further, polarization optics are optionally used. Another way to provide sufficiently long path lengths, large depth of field, and good image quality is to use a telescoping frame or further fold mirrors. The path lengths can be extended by mirrors on or near the exterior portions of the frame that are moved, or on another movable component. Therefore, the present device according to the application avoids a disadvantage in many prior art designs—having a high f-number final lens in a position such that the pupil plane reflection is sampled in the retinal plane. Therefore, the present device does not produce images which result in a bright, unwanted reflection in the image of the retina.

In the device according to the present application, the focusing mechanism is optionally kept simple to minimize complexity of use, size, and weight. Focusing may be achieved by increasing or decreasing the relation of retinal and pupil planes (the desired focal plane and the entrance plane) by the use of one or more movable mirrors and/or lenses, such as shown in FIG. 3. These components may be operable by either mechanical or electrical control. In one embodiment, a movable lens or lens array is provided, as well known in the art. The moving mirror or lens can be operated manually by, for example, a rotating knob operated by a single finger or thumb, by grasping a rotatable lens housing, in a manner similar to a camera, by a slide switch, or any other mechanical positioning device known in the art. Optionally, the moving mirror or lens can be motorized, preferably using a battery-powered DC motor. Optionally, an AC motor can be used if there is a connection to an external AC power supply.

According to one aspect of the present application, proper focus can be found through visually inspecting images on a display; by using an indicator to locate the brightest reflection returning from the target (without necessarily having to provide visualization of the data); or by using lower resolution images, or a small number of images acquired more rapidly, up to video rate, to find the focus quickly, after which an image having a better resolution is provided. The focus can be a manual mechanism or an autofocus mechanism well known in the art. Finally, the focus can be determined based on all or a portion of the image.

According to one aspect of the present application, the device may include a display on which the user can see the image, such as a liquid crystal display (LCD). However, because an onboard LCD adds weight, may be fragile, and draws current, it may be desirable in some embodiments to eliminate a display and provide only a focus indicator. As noted above, when the retina is in focus, this layer provides the greatest light return throughout the visible spectrum and near infrared. Therefore, according to one aspect of the present application, an image can be focused by positioning the image on the anterior segment to decrease this signal, and the focal plane to sample the retina adjusted to the maximum brightness. Thus, while an image is useful for focusing, with a large depth of field, an indicator may optionally be used. The indicator may be a display, a light when a criterion is reached, a light that gets brighter or dimmer corresponding to the amount of light received, a dial, a digital read-out panel, a sound, a needle display, or any other element that can provide a signal to the user that focus has been obtained.

The device may optionally include a display for viewing the image after its acquisition. The display may be a liquid crystal display (LCD) or other suitable display device. The image data may be transferred by USB, IEEE 1394, a wireless protocol, or other connection to a device or computer, as is well known in the art. The device may further optionally include one or more onboard memory devices, either in the integrated circuits or a removable memory device or film that can be transferred to an external viewing device such as indicated at 44 in FIG. 2. The data may be transmitted by either wire or wireless methods to a receiving device, such as a computer, personal desk assistant, cell phone, or other device.

According to yet another embodiment of the present application, to view structures in a plane not conjugate to the retina of the eye, modifications can optionally be made by a focusing assembly as shown by lenses 60 and 64 in FIG. 3. A further lens or mirror assembly may be added, existing lens or mirrors removed, or other lenses or mirrors substituted for the focusing assembly, as will be appreciated by one of ordinary skill in the art. These structures include the anterior segment of the eye, but are not limited to ocular structures and could include skin or any other biological or non-biological structure. The narrow entrance pupil and the separation of illumination and detection pathways distinguish this design from an optical confocal microscope device intended for optical sectioning with the highest axial resolution, although the embodiments shown in FIGS. 3-8 allow for an instrument with some optical sectioning capability, i.e. an instrument that could be used as a microscope or general purpose imaging device of modest resolution and rejection of out of plane remitted light. The focusing elements as shown can optionally be used to provide an image that enlarges the view of a target, and further enlargement of an image for viewing occurs largely electronically, thus broadening the potential uses beyond that of the human retina or eye as a whole. According to one aspect of the present application, the scanning of the illumination source with respect to the target provides an image of higher contrast than does typical flood illumination or illumination from existing and external sources such as daylight, and in this way broadens the potential uses of the device beyond the scope of the human retina or eye.

According to one aspect of the present application, there are several structures in the anterior segment of the human eye that may be imaged by using ancillary or substituted focusing elements that are not in the focal range of the digital retinal imaging device of the present application. For example, the device according to the present application could be used to image corneal trauma or disease, results from corneal surgery or refractive laser surgery, a foreign body in or on the eye, a chemical injury or burn, iris neovascularization, exterior ocular injuries, burns, contact lens fit, external inflammation, infectious disease, tear duct problems, lid lesions, pterigeum, scleral or iris vessel problems, or other data needed to document the emergency or health status of a patient.

In addition, it should be noted that the device as described may be optionally housed in a casing. Further optionally, controls, such as an on-off switch and a focusing control, may be accessible through the casing. The casing may be rugged and lightweight and encloses all the optical and electronic components described above. In addition, a head or chin rest can be optionally provided, and may be configured to allow a patient to hold the eye in a steady manner in alignment with the device. The head or chin rest may be operable to telescope to form a readily packed and carried portable device. In another embodiment, the head or chin rest can be folded to form a compact footprint. A further embodiment has a casing that is held by the user in a manner similar to a consumer digital camera or video game. A viewfinder may be provided for locating the eye. A control on the casing can act as a toggle switch for off and on and for various modes or resolution of image acquisition.

A number of embodiments of the present device have been built and tested to determine the feasibility of obtaining acceptable eye images safely and under battery power with the capability of transferring images to a remote source. A number of embodiments were tested using a model human eye, as known in the art. The model eye was used to determine that the device is able to operate and obtain an image using an acceptable amount of light that is consistent with eye safety. The relative amount of light in the model eye has been calibrated to the human eye and is known.

An embodiment similar to that described above in FIGS. 2 and 3 was built and tested on a human eye, after obtaining required regulatory approval. Suitable images of the retinal plane of a human eye were obtained at an appropriate resolution, having good contrast, and with no strong reflections from the corneal planes. Features known to be unique to the particular human eye tested were recognizable.

This application is particularly applicable within the fields of opthalmology, optometry, emergency services, military ocular screening, ocular screening in any mass situation, health care workers providing diagnoses at locations remote from eye care specialists, telemedicine, and eye examination by persons without specialty eye care skills, such as pediatricians, ER technicians, or family practitioners. A primary application of the device is for use by, for example, emergency personnel, when there is a suspicion of trauma to the eye. In such situations, it can be helpful to know if an individual with a suspected eye injury can be allowed merely to rest for a period of time or if, instead, the patient requires further emergency treatment. A further application is the remote or mass screening for potential eye disease by personnel who are not primarily specialists in the eye, such as pediatricians or family practitioners, and also including workers who have minimal medical experience and lack instrumentation or computer expertise. The device has a minimum of controls, which provides simplicity in operation, so that a high degree of training is not required to operate the device.

In contrast to the present invention, current commercially available scanning laser opthalmoscopes are too large and expensive for use as a portable device in the field. Further, these devices are complex and require a user to be highly trained both in using the device and in reading the resulting ophthalmic images. The striking image quality of the large SLOs and the sectioning capabilities of tomographic devices, which spoil the signal to noise ratio, are not needed in the present device.

In other embodiments of the present application, a device may utilize 3 or more light sources to illuminate the target with different wavelengths that will enhance the visibility of certain features. Imaging can optionally be performed with a device having one, two, three, or more such light sources, with each source differing to provide unique and beneficial properties, such as a different wavelength, increased power, or different polarization properties. Light sources can optionally be controlled by the control electronics 46 (see FIG. 2), for example, to turn on and off, to operate in a steady state mode or a flash mode, or to control intensity of the light, as discussed further below. The light from each illumination source can optionally undergo beam shaping prior to being directed towards additional elements in the optical imaging system.

According to yet another embodiment of the present application, light from illumination sources can be directed with turning mirrors, and then combined into a single beam with beam combining elements, in a manner known in the art, published by the inventor. See, e.g. Elsner et al, 1992. Such combining elements can be reflective and transmissive elements; can be dichroic mirrors to take advantage of the wavelength differences of the illumination sources; or they can reflect or transmit according to polarization properties of the illumination sources. According to one embodiment, each of the illumination sources is combined to the next by a pair of beam combining elements. For example, a first element, such as a mirror, steers the beams and a second element combines the two beams and further steers one or the other beam. The position of the combining elements can be configured to minimize the space taken by the device or light efficiency, rather than configured for ease of optical alignment.

According to one aspect of the present application, intensity of the light from the sources may be controlled in any suitable manner if desired, such as to decrease the level down from the FDA approved level for continuous viewing. The intensity of the light can also be controlled electronically, via neutral density filter or color filter, mechanically, in which case slit 56 in FIG. 3 represents an adjustable slit or iris diaphragm that may be controlled mechanically. The illumination control device may thus be operated mechanically or electronically, such as with a finger operated screw. The intensity of the light can also be increased or decreased with a polarizing element. Alternately, adjustment of the intensity of the illumination light uses electronic control from the control electronics, such as that depicted in FIG. 2, an ancillary detector or the output from the detector array 68 in communication with the light sources or the intensity control element to can be used adjust power, voltage, or current. A detector gain control can be used as well to increase or decrease contrast.

In an exemplary embodiment using three illumination sources, such as shown in FIG. 4 of the prior patent family, illumination sources included a Helium-Neon ("HeNe") laser at 543 nm, a diode laser at 830 nm, and a vertical cavity surface emitting laser ("VCSEL") at 850 nm. Illumination sources such as Diode lasers and VCSELs can readily be operated using direct current and can thereby be operated by one or more batteries. Battery operation allows the optical imaging device to be portable and used in remote locations. By using two or more sources that differ in the amount of absorption of features of interest, such as the blood in a hemorrhage, it is possible to use image comparison as in FIG. 8 to enhance the detection of such features.

In this embodiment, the VCSEL is of unusually small size for an illumination source in an optical imaging instrument, as VCSELs are typically used in communications and optical computing, not optical imaging instruments. The footprint of the device using this source is thus more compact, and the weight is reduced compared to conventional imaging devices. The energy efficiency of the VCSEL, being unusually high, as well as the possibility of utilizing direct current such as from a battery, also assists in reducing the weight and footprint of the present imaging device. This diameter of the laser element of a VCSEL can be as small as 50 microns, plus the associated housing and beam shaping elements that are larger; the total package except for the power supply is approximately the size of a small integrated circuit or transistor in a can mount. In this context, the VCSEL, is merely one more electronic component in the circuit. The high energy efficiency permits the output to be in the low mW range when using a single battery, such as a 9 V battery plus current limiting circuitry.

Diode laser illumination source is of an intermediate size and provides an intermediate footprint and weight, and also supports the possibility of battery operation and remote use. Any infrared or near infrared source having an appropriate size, energy efficiency, power density, beam quality, and weight can be used as an illumination source to replace the sources described above. As sources with high coherence lead to interference artifacts in the slit that is scanned, these are less desirable unless these unwanted artifacts can be reduced so that there are not illumination differences along the length of the scanned slit. Superluminescent diodes are one type of source that can be used to provide low coherence.

When the target is the human eye or other substance that remits near infrared or infrared light, the target can be viewed with a safe and (where applicable) comfortable amount of illumination, using illumination sources either a laser diode or a VCSEL. A near infrared source is important for penetrating thin blood layers and the lens with cataractous changes. Near infrared sources, when used to image the retina, do not lead to constriction of the human pupil, thereby providing sufficient illumination to use the imaging device in a non-mydriatic manner, with either flashed or steady-state illumination. An illumination source with near-infrared wavelength having a beam of acceptable quality produces an image of acceptable quality when used in a scanning system, such as those depicted in FIGS. 2 and 3. The imaging device can be limited to use with a near infrared source for use in an environment of daylight, room light, or other visible wavelength light by positioning a filter blocking the visible wavelength light, using any suitable position, where the light is approximately in a plane optically conjugate with the plane of target 52 of FIG. 3, such as between the target 52 and a focusing lens 64 in FIG. 3.

According to one embodiment, the illumination source 54, as depicted in FIG. 3, can be of a shorter wavelength than sources in the near IR range. Examples include, but are not limited to, HeNe lasers, wavelength sources such as lamps and light emitting diodes of sufficient power density and beam quality to permit scanning of a slit of uniform intensity across the target, as would be known by those of skill in the art. In the eye and other biological tissues, the use of a shorter wavelength, specifically in the range of 514 to 594 nm, enhances the contrast of structures containing blood, but can lead to constriction of the human pupil. However, it was recently found that with sufficient contrast, these features are visible in near infrared light, possibly to a greater extent than that needed for screening for disease. For the detection pathway to utilize a modest cost detector array, it is necessary to use a sufficiently bright source to provide an image despite this constriction. However, a light source of short wavelength can be used in a flashed mode, following alignment of the target and the imaging device using a near infrared illumination source. An example in the human eye is the detection or management of diabetic retinopathy. Similarly, for reflectance or fluorescence imaging, a light source of one wavelength range can be used for alignment prior to imaging to prevent excessive light exposure, thermal changes, or photobleaching. In the eye three examples are fluorescein angiography and fluorophotometry in the retina and vitreous, and fluorescein staining for assessment of tear film quality for the anterior segment.

In one embodiment, a laser scanning digital camera device features the ability to scan one or more light sources. Further each light source is specifically designed for detection of target characteristics according to a specific configuration of wavelength, beam shaping, illumination aperture, spatial or temporal modulation of the beam, polarization content, or structured illumination. By way of nonlimiting example, if scanning with a slit, structuring the illumination with a square aperture is optionally used to provide even illumination across the image. When even illumination is provided, target detection at any location within the field of view is possible.

According to one embodiment of the present application, the electronic aperture is synchronized in a closed loop manner with the active period of the detector. This loop may be closed by prior calibration, in situ calibration, or while operating the device. The synchronization may be determined by a master signal, the scanning element, or the detector. In one embodiment, the master signal may be generated by a read-out of the position of the scanning element. The position signal may be generated when the light from the moving scanning element reaches a detector, and this signal can indicate the beginning of the image or the position within the image for even more precise control, with the detection of light returning from the target synchronized with respect to the position on the target of the illumination. This allows the device to obtain images while using exceptionally low cost optical elements that serve as mirrors in the scanning element, since the scanning slit overfills the target pathway in the direction perpendicular to the scan and the timing in the direction of the scan is variable in a rapid and accurate manner. Synchronization of the scanning element to the target that is performed on portions of the image provides rapid flexibility of aperture position.

According to another embodiment of the present application, the digital image device is operable to provide a high quality image by using a series of images acquired in succession rapid enough to allow the adjustment of position of the target and instrument with respect to each other. In addition, according to certain embodiments, the images are assessed for quality and improved by the adjustment of parameters used in image acquisition. The adjustment is made more readily when the series of images is acquired in rapid succession. The adjustment is made by software, electronic circuitry, or the operator, or a combination thereof. Optionally, the digital imaging device is further capable of providing onboard or embedded control of parameters. The same control mechanism is optionally in communication with electronic circuitry or a computer with sufficient memory to allow storage of images so that selection of the highest quality images can be performed immediately after acquisition. In a moving target such as an eye, or one that is changing over time, this provides a greater probability that an image of acceptable quality is obtained. In the embodiment with a unskilled user, the acquisition of images can be adjusted to incorporate sufficient time and number of images, and requiring little action on the part of the user, to improve the chance of acquiring suitable images. The control mechanism can have the capability of processing aspects of the image to assure quality control. The control mechanism is optionally capable of performing processing on the images and then displaying and storing these images.

According to one embodiment of the present application, the digital imaging device is operable to provide high contrast of features that may be used to identify a target or portions of the target that allow improved detection of the target itself, particularly in the case of a moving or changing target, or regions of interest within the target. In the embodiment, a wider field of view for imaging the retina is possible, and more precise localization of the regions within the retina becomes possible because two main features, such as the fovea and the optic nerve head, are now potentially within the field of view with sufficient spacing that localization is improved over identifying a single feature that is used in current high rate retinal tracking devices with and without polarization. In the embodiment with polarized light illumination, there is the potential for using the macular birefringence and the optic nerve head birefringence to identify two points within the retinal image of sufficient spacing to localize retinal features. The use of the electronic aperture further improves the detection of the macular and the optic nerve head birefringence by rejecting unwanted scattered light that does not contain polarized light information, but allowing sufficient light to be detected to provide a robust signal.

In the embodiment with reflected light illumination, there is the potential for using the macular and the optic nerve head features to identify two points within the retinal image of sufficient spacing to localize retinal features. The use of the electronic aperture further improves the detection of the macular and the optic nerve head features with sufficient contrast by rejecting unwanted scattered light that reduces image contrast, but allowing sufficient light to be detected to provide a robust signal.

In the embodiment with polarized light illumination, there is the potential for using the macular birefringence and the optic nerve head birefringence to identify two points within the retinal image of sufficient spacing to localize retinal features. The use of the electronic aperture further improves the detection of the macular and the optic nerve head birefringence by rejecting unwanted scattered light that does not contain polarized light information, but allowing sufficient light to be detected to provide a robust signal.

According to another embodiment of the present application, one or more optical channels can added to the digital device to provide images using illumination differing in wavelength, beam shaping, illumination aperture, spatial or temporal modulation of the beam, polarization content, or structured illumination. The additional optical channels provide the possibility of viewing with the wider field and low cost digital device, with a flexible electronic aperture, and simultaneously providing an image with different information content or providing a visual stimulus or alignment beam. In one embodiment, the visual stimulus is used to direct the position of the retina. Additionally, the stimulus is optionally used to elicit a response for diagnostic or experimental use with humans or in situ use in biological preparation. In one embodiment, the wide field with the scanned slit illumination is of sufficiently long near infrared wavelength, low power, and low duty cycle to be rendered nearly invisible to the human eye. Such conditions do not interfere with a visual stimulus or lead to heating in the retina or a biological preparation, but provide localization of the stimulus or illumination impinging on a preparation.

FIG. 9 illustrates an embodiment, which describes a group of configurations, in which a single scanning element 50 directs light from one or more light sources and shaping optics 54 to a target 14 but not the light remitted from the target 14. The light from an illumination source 154 undergoes beam shaping by lens 155 and passes through square aperture 156 to ensure even illumination in one dimension when passing through cylindrical lens 157 and a slit aperture 56, conjugate with the target 14. These elements 154, 155, 156, and 157 together correspond to element 54 in FIG. 2. According to one configuration, illumination from an illumination source 54 utilizes beam shaping optics well known in the art that change illumination from quasi-Gaussian to a slit output. This change in illumination may be accomplished by using a cylindrical lens in the illumination pathway prior to the slit 56. However, if edge emitting illumination devices or other linear devices are used, a cylindrical lens may prove unnecessary. Slit aperture 56 is illustrated in more detail in FIGS. 5-8, and as described above. As can be seen in the figures, slit 56 has a long axis orthogonal to the plane of the figure.

In FIG. 9, the light passing through slit aperture 56 is directed by a focusing element 58 onto the scanning element 50. The scanning element 50 rotates or oscillates to reflect the light sequentially across the target in a direction perpendicular to the long axis of slit aperture 56. Throughout the figures, lines exiting the scanning element 50 indicate an illumination path. From the scanning element 50, the light is then directed by one or more focusing elements 60, here shown as a movable lens 164 to focus the light through a narrow angle of entrance, (e.g., the pupil) 62 in FIG. 3. The light is further focused by focusing elements 161 and 162, corresponding to 64 in FIG. 3, and bright the light to a focus at the target 14 (e.g., the retinal plane). FIG. 9 illustrates the entrance and focal planes schematically only; see FIG. 1 for greater detail. The light at slit aperture 56 is in an optical plane conjugate to the target 14. The light at scanning element 50 is in an optical plane conjugate with the plane of the narrow angle, just anterior to the lens 24, shown in FIG. 3 as a narrow angle of entrance 62. A focusing element 164 is preferably mounted for movement in an axial direction to allow focusing of the light on the target 14. When imaging a target without a lens (e.g. a target other than the human eye with a functional lens), focusing element 164 is optionally a set of lenses suitable for focusing on the target 14, along with additional lenses 161 and 162. The wide field of view illustrated in FIG. 9 is improved by the use optical design specialized for wide field, illustrated here as a Kellner type of ocular mounted near the eye, formed by optical elements 161 and 162, or the use of an ophthalmic lens that is aspherical. In addition, the wide field of view requires sufficiently large diameter lenses or mirrors to allow a free zone that passes the weak signal returning from the human eye, in particular focusing element 164.

As noted above, scanning the light across the target 14 through a slit aperture (and scanning again in the detection pathway if this is performed, described further below) aids in decreasing unwanted scattered light in the resulting image. The scanning can be accomplished in a variety of ways well-known in the art in addition to the method in FIG. 9.

In the optical pathway between scanning element 50 contains one or more separation elements 66, 266, and 366, to direct additional optical pathways in or out of the main pathway. Separation element 66 in FIG. 9 corresponds to separation element 66 in FIG. 3, and may consist of various reflecting or transmitting configurations. Separation element 266 introduces a second optical channel of illumination. An illumination source 254 and its beam shaping optics 255 may differ in wavelength, power, spatial or temporal properties, beam shape, focus, polarization characteristics or any of a number of other properties. Light from illumination source 254 is focused by focusing element 255 and directed towards a target by separation element 266, passing through focusing elements 164, 162, and 161.

Light from illumination sources 354 is directed towards the target, starting from a position outside the main optical pathway, shown here as directed towards the anterior segment of the eye and not towards target 14.

Light returning from the target 14 is separated from light striking the target at separation element 66. In the embodiment shown in FIG. 9, separation element 66 is illustrated as a mirror that does not alter the course of the light directed towards the target 14 on the illumination pathway, but instead directs the light returning from target 14 into a detection pathway, illustrated as solid and darker gray lines. The light remitted from the target 14 in the detection pathway is focused by a focusing element 74 and directed to a detector array 68. The focusing element shown here is a mass produced and inexpensive camera lens, a double Gauss, but for our monochromatic images a lens of less complexity is also suitable. The detector array 68 is conjugate to the plane of the target 14. As in FIG. 3, a wide range of combinations of separation elements 66 also comprise a beam splitter with the reflective portion intersecting the beam of light directed at the target 14, with the transmissive portion directing light remitted from the target, or any other combination of elements as described concerning FIG. 2 above to separate the light from the illumination pathway from that remitted from the target 14 and direct the remitted light towards the detection pathway. Separation element 66 optionally contains additional mirror surfaces to direct the light in a direction convenient with respect to the configuration of the other components, thereby allowing crowding of components near the target 14 to be reduced. Further, additional mirror surfaces may be used and configured to reduce component crowding near mounting surfaces of focusing elements 160, 161, and 164, or to prevent components from interfering with the motion of either focusing element 164 or scanning element 50 by spatially separating the light directed towards the target 14 from the light returning from the target, unwanted, direct reflections from focal planes not in the plane of the target can be eliminated by minimizing the spatial overlap at beam separator 66. With respect to the target, the illumination is directed at the target from a slightly different position than is the detection pathway from the remitted light so that there is minimal spatial overlap between the detection and illumination pathways, thereby minimizing any unwanted reflections of optical elements, including those often found in association with the target such as the cornea and lens of the human eye when the retina is the target (see FIG. 1).

The separation element 66 may comprise a partially or fully reflective surface that does not intersect the light directed towards the target 14. The reflective surface may comprise a mirror or a beam splitter with the reflective portion not intersecting the beam of light directed at the target, as shown. The separation element can also be any number of other separation elements, such as a beam splitter with a reflective portion intersecting the beam of light directed towards target and a transmissive portion including a mirror that reflects less than 100% of the light towards the target or a transmissive portion intersecting the beam of light directed towards the target and the reflective portion allowing the light from the target to pass.

According to one embodiment of the present application, further decrease of light from unwanted planes can be obtained by directing the light on the detection pathway from the target 14 to one or more two-dimensional detector arrays 68 comprising a complementary metal-oxide-semiconductor chip ("CMOS" or "CMOS detector array"). The detector array 68 is in synchrony with the illumination timing and of a suitable sensitivity at the wavelength or wavelengths of light returning from the target to allow detection of light returning from the target. The detector array 68 may detect light returning from the target from illumination source 154 or 254. A similar detector array 368 detects the light that is returned from a target, such as the ocular lens 24 or pupil 16, directed by separator element 366, and focused by focusing element 374 onto detector 368.

The combination of illumination sources and beam shaping optics shown in FIG. 9 may be incorporated with further devices such as polarization generation devices, temporal or spatial filters, and position manipulators to use the scanning engine and flexible electronic aperture to build imaging devices for not only reflected and multiply scattered light, but also structured illumination for enhanced detection of targets and stereogrammetry, polarimetry, fluorescence imaging, and stereo imaging.

A target image provides a variety of features, and to localize these better than methods using rotation or translation about a single point, two references may be used. The macula and the optic nerve head are two such major features that can be used to localize or stabilize features in the retina, for the birefringence signal radiating from the macula and the birefringence signal from the nerve fiber bundles radiating from the optic nerve head.

The illumination striking the target may be patterned, and a pattern such as stripes provides a convenient method for generating the pattern. Illumination sources, such as those shown as 154 or 254 in FIG. 9, can be temporally modulated to produce stripes as they sweep across the target 14. Use of a Vertical Cavity Surface Emitting Laser as an illumination source provides the capability for rapid modulation without additional wear and tear, as do Light Emitting Diodes and other modulatable sources or sources fitted with temporal modulating devices such as choppers or shutters.

When operating the LSDC in closed loop mode, the scanning element 50 in FIGS. 2 and 9 can be operated as either the master or the slave. One method of synchronization, is to use the a motor encoder on scanning element 50 in FIGS. 2 and 9. The encoder can be used either as a signal to provide a master signal for synchronization or as a signal to provide improved scanning element 50 positioning and rate.

In one embodiment of synchronization of the image acquisition by detector array 68 to the scanning element 50, the scanning element 50 serves as the master, and the detector array 68 synchronized to it by means of a Start of Scan with a fixed point, ancillary detector. In a point scanning system, a Start of Scan is typically used for synchronization in one direction, but must be further synchronized with the scanning element in the orthogonal direction, and does not readily offer the possibility of lessening the tolerances on the position and timing of the components in a unitary scanning element 50. In a slit scanning system, such as that shown in FIGS. 2 and 9, this allows lower cost in an obvious manner. The start of scan also permits timing out the illumination source 154 or 254 for safety and power efficiency. In one embodiment, the start of a scan has a series of components and signals, with the scanning element consisting of a polygon mirror on a DC motor, serving as the master for the synchronization. The detector can be a pin diode, or other detector, placed at the edge of the retina plane A digital trigger signal may optionally formed. A delay may also added, which can be made adjustable by means such as a potentiometer, to allow for variable offset of the illumination reaching the position of the diode. This allows adjustment of image acquisition to be in synchrony with the illumination slit, or to be offset to provide multiply scattered light imaging. A start of scan signal can be formed, which can be TTL, and the start of scan signal is sent to the sensors.

In one alternative method of synchronization of the scanning element 50 in FIGS. 2 and 9 as the master, a detector array, such as a two dimensional CMOS detector can be used, rather than a single point detector. The position of the CMOS detector is adjacent to the retinal plane, with the advantage that the alignment to the detector array used in imaging is straightforward, and potentially of lower cost than adding an additional circuit. The frame rate of this synchronization method can be made very high, an advantage in that the synchronization can be made more precise. The gain of the detector array, such as when using a CMOS detector, is readily controllable, unlike the typical Start of Scan with the fixed point detector. The arrival of the illumination slit is detected at the leading edge of the image and then checked to maintain it within the appropriate region of interest, mandated by the position to be acquired by the electronic aperture. A Start of Scan signal is determined from the predicted arrival of illumination at the leading edge of the image, then a line trigger is generated for image acquisition at the appropriate time for each line or group of lines on the detector array.

The description above pertains to several illustrative embodiments of the invention. Many variations of the invention may be envisioned by one skilled in the art. Accordingly, such variations and improvements are intended to fall within the compass of this disclosure. The invention is not to be limited by what has been particularly shown and described, except as indicated by the appended claims. The aim of exceptionally low cost, low power requirements, smaller size, and ease of use can be applied beyond the use in the eye field. For instance, it will be appreciated that embodiments of the present application can be used as a general imaging instrument, a microscope, or an endoscope. The embodiments for eye applications include diabetic retinopathy, age-related macular degeneration, macular hole, epiretinal membrane, glaucoma, contact lens problems, ocular inflammation, infectious diseases, ocular trauma, and other conditions. An all-in-one device with increased ease of use that allows simultaneous or nearly simultaneous images of both the anterior segment and posterior segment of the eye that are readily viewed, stored, or transmitted would be greatly appreciated.

Further, embodiments of the present application can also be used as a general imaging device, or for microscopy, to improve image detection of targets and potentially decrease the light level needed for image formation. When used with a scanning element, certain of the above embodiments efficiently use light and decrease the potential for unwanted scattered light. For the purpose of developing imaging applications, it is not often known with certainty how much light will be collected from the target and the characteristics of that light. The electronic aperture capability, in an optical plane conjugate to the target plane, helps control the sampling of light. The aperture allows the detection of reflected or multiply scattered light to varying degrees in a rapid manner and without mechanical parts. Similarly, the electronic aperture can be rapidly adjusted to emphasize contrast, such as by reducing the aperture size to detect mainly reflected light, or increase signal-to-noise ratio, such as by increasing aperture size to obtain more total light. Thus, the electronic aperture provides more flexibility in sampling the light, which allows an optimal setting to be determined for a naïve user for each application. A user or instrument developer can select the setting in an unusually flexible and rapid manner, according to the needs of each application. One such use is in the field of infectious disease, in which dark field imaging has already been shown to be advantageous for the detection of malaria because it allows unstained blood to be tested (Jamjoom G A. Dark-field microscopy for detection of malaria in unstained blood films. J Clin Microbiol. 1983 May; 17(5):717-21.) The use of an embodiment of the present application optimized to take dark field imaging has the advantage of less handling of blood or other substances that may pose additional health and safety issues, as well as requiring less expertise and equipment in slide preparation. A device that detects important targets such as blood-borne diseases requiring less expertise and cost would be greatly appreciated.

Further, additional embodiments include optimizing the illumination light to detect a target for use with the electronic aperture. This optimization may take place in the selection of wavelength, beam shaping, illumination aperture, spatial or temporal modulation of the beam, polarization content, or structured illumination. This allows use for a broad range of applications and rapid, less expensive prototyping for applications. Such a low cost device that is flexible and easy to use, and far lower in cost than producing and aligning a series of mechanical apertures, and can be optimized readily according to the application and the illumination source, and has equivalent or improved detection of a target, would be greatly appreciated.

Yet another embodiment of the present application includes having more than one pathway for detection of light, each of which can utilize the electronic aperture. The additional detection pathways can differ in plane of focus, angle of incidence or regard, wavelength detection or filtering, sensitivity or gain, temporal or spatial properties, resolution, or polarization properties. Additional detection pathways allow optimization at reduced cost in instrumentation such as an all-in-one device for anterior and posterior segment of the eye, simultaneous confocal fluorescence and reflectance imaging, confocal multispectral imaging, stereo in the plane of choice, simultaneous detection of reflected and multiply scattered light, polarization imaging, and imaging techniques that require synchrony with target excitation or two or more detection channels. Such a device allows a more flexible means for providing near simultaneous observation of directly backscattered and multiply backscattered light than described in U.S. Pat. No. 6,236,877 and related work. As such, a low cost device that is flexible and easy to use, or that can be optimized readily according to the application, and has equivalent or improved detection of a target due to the use of two or more detection pathways would be greatly appreciated.

What is claimed is:

1. A digital retinal imaging device comprising:
a. an illumination source;
b. a scanning element operable to move a portion of an illumination pathway created by the illumination source with respect to a target;
c. at least one slit within the illumination pathway of the illumination source; and
d. a two dimensional complementary metal-oxide-semiconductor ("CMOS") detector chip having a rolling shutter functionality.

2. The digital retinal imaging device of claim 1, wherein the device lacks a lens array and mechanical aperture.

3. The device of claim 1, further comprising an electronic or mechanical aperture within the illumination pathway operable to shape the illumination pathway.

4. The device of claim 1, wherein the illumination pathway is shaped by increasing or decreasing the width of a slit aperture, thereby resulting in an improved image quality for a resulting confocal image, multiply scattered light image, or sharpened image.

5. The device of claim 1, wherein an electronic aperture and a two dimensional detector array replaces the CMOS with rolling shutter.

6. The device of claim 1, wherein the illumination source is an infrared illumination source.

7. A digital retinal imaging device comprising:
a. an illumination source and scanning element operable to move the illumination source with respect to a target;
b. a detector array operable to detect and build a first image data set relative to the target, and further operable to detect and build a second image data set relative to the target;
c. a processor operable to utilize the first image data set and the second image data set such that each line comprising the first image data set is compared to a corresponding line on the second image data set in a weighted manner such that a sharpened image is created.

8. The digital retinal imaging device of claim 7, wherein the detector array is a complementary metal-oxide-semiconductor.

9. The digital retinal imaging device of claim 7, wherein the processor is further operable to utilize the first image data set and the second image data set such that each line comprising the first image data set is combined with a corresponding line in the second image data set in a weighted manner such that an improved signal to noise ratio is obtained by increasing a sampled area imaged by the device.

10. The device of claim 7, further comprising an electronic or mechanical aperture within the illumination pathway operable to shape the illumination pathway.

11. The device of claim 7, wherein the illumination pathway is shaped by increasing or decreasing the width of a slit aperture, thereby resulting in an improved image quality for a resulting confocal image, multiply scattered light image, or sharpened image.

12. The device of claim 7, wherein an electronic aperture and a two dimensional detector array replaces the CMOS with rolling shutter.

13. The device of claim 7, wherein the illumination source is an infrared illumination source.

14. A digital imaging device comprising:
a. an illumination source and a mechanism to cause a scanning motion of the illumination with respect to a target;
b. a CMOS array operable to select one or more leading lines or lagging lines with respect to the alignment with an optical axis of a beam from the illumination source;
c. a processor operable to combine the one or more leading lines and lagging lines selected and detected to create a multiply scattered image.

15. The device of claim 14, further comprising an electronic or mechanical aperture within the illumination pathway operable to shape the illumination pathway.

16. The device of claim 14, wherein the illumination pathway is shaped by increasing or decreasing the width of a slit aperture, thereby resulting in an improved image quality for a resulting confocal image, multiply scattered light image, or sharpened image.

17. The device of claim 14, wherein an electronic aperture and a two dimensional detector array replaces the CMOS with rolling shutter.

18. The device of claim 14, wherein the illumination source is an infrared illumination source.

19. The device of claim 14, operable to combine wherein the one or more leading lines and lagging lines are combined in a weighted manner.

20. The device of claim 19, wherein the one or more leading lines and lagging lines selected and detected are combined into an image in a weighted manner to obtain a confocal image.

21. The device of claim 20, wherein the resulting image is further modified by weighting the one or more leading lines and lagging lines in such a manner that signal to noise ratio, image contrast, and/or other image quality variables are maximized.

22. A device for digital retinal imaging, comprising:
a. an illumination source that fluoresces when excited, and operable to produce an illumination pathway;
b. a first detector array within the illumination pathway operable to detect wavelengths of irradiated energy reflected from a target within the illumination pathway;
c. a barrier filter operable to reject selected wavelengths such that only selected wavelengths reach the detector.

23. The device of claim 22, further comprising a second detector array operable to be synchronized to the first detector array such that stereo imaging, polarimetry and simultaneous indirect light imaging with a leading and lagging electronic aperture can be performed.

* * * * *